US00PP22034P2

(12) United States Plant Patent
Warren

(10) Patent No.: US PP22,034 P2
(45) Date of Patent: Jul. 19, 2011

(54) SUGAR MAPLE TREE NAMED 'JFS-KW8'

(50) Latin Name: *Acer saccharum*
Varietal Denomination: JFS-KW8

(75) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 12/798,427

(22) Filed: Apr. 2, 2010

(51) Int. Cl.
*A01H 5/00* (2006.01)

(52) U.S. Cl. ..... Plt./224
(58) Field of Classification Search ..... Plt./224
See application file for complete search history.

(56) References Cited

U.S. PATENT DOCUMENTS

PP2,339 P 1/1964 Flemer, II
PP11,119 P 11/1999 Lamis

*Primary Examiner* — Annette Para
(74) *Attorney, Agent, or Firm* — Klarquist Sparkman, LLP

(57) ABSTRACT

A variety of sugar maple which combines unusually dark green summer foliage and bright red fall color with an upright branch orientation, straight trunk, and narrowly oval to oval canopy shape.

8 Drawing Sheets

Latin name of the genus and species of the plant claimed: *Acer saccharum.*

Variety denomination: 'JFS-KW8'.

BACKGROUND OF THE INVENTION

During the fall of 2000, I searched for improved varieties of sugar maple, *Acer saccharum*. I examined several thousand seedling trees of *Acer saccharum* growing in rows at a nursery in Boring, Oreg. I found a number of seedling trees that differed from typical seedlings. One tree, which was three years old at the time, particularly caught my attention. My attention was drawn to this tree because it was taller and stronger growing than any other seedling in the field and also displayed unusually bright red fall color. I tagged it and transplanted it during the winter into a testing block for further evaluation. I evaluated this tree every year thereafter and determined that it was superior to typical seedlings in several features.

In order to test this tree under nursery growing conditions, my new tree was test propagated by T-budding onto *Acer saccharum* rootstock in small plots of 10 trees in 2002, 2003, 2005, and 2006. This asexual propagation in Boring, Oreg. by budding on *Acer saccharum* rootstock has shown that the characteristics of my new tree are firmly fixed in successive generations. I evaluated each plot of these test trees for three years in the nursery and then discarded all but 15 which I re-planted in 2008 and 2009. Testing, evaluation, and comparison with seedlings of the species as well as with existing commercial varieties of *Acer saccharum* has convinced me that my new tree has superior growth and appearance characteristics for landscape use.

SUMMARY

This new cultivar possesses a unique combination of characteristics in that it combines unusually dark green summer foliage and bright red fall color with an upright branch orientation, straight trunk, and narrowly oval to oval canopy shape.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
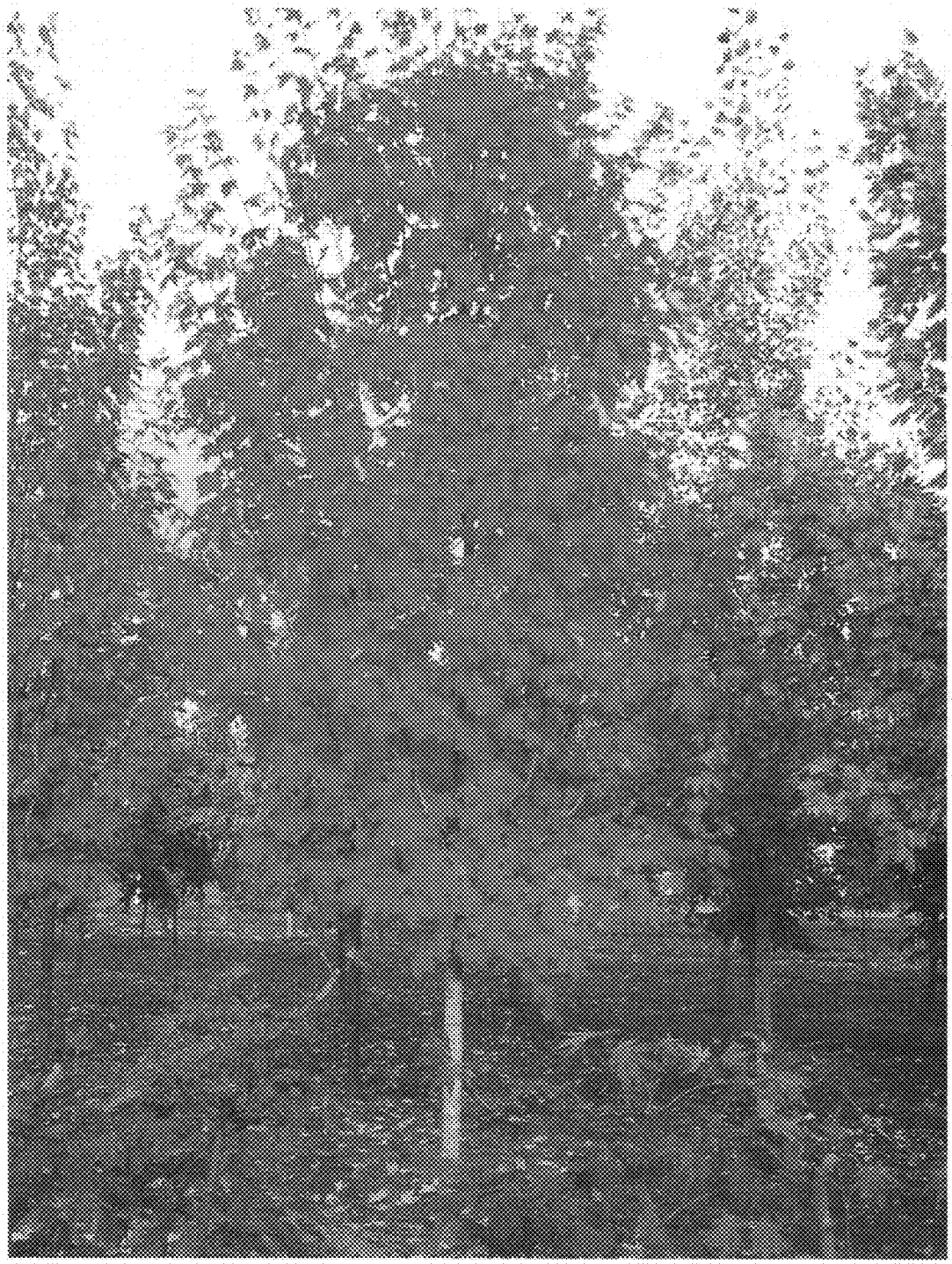
FIG. 1: Shows the original tree in autumn, illustrating the upright growth habit, straight trunk, bright red fall color, and the narrow oval to oval form.
Figure 2:
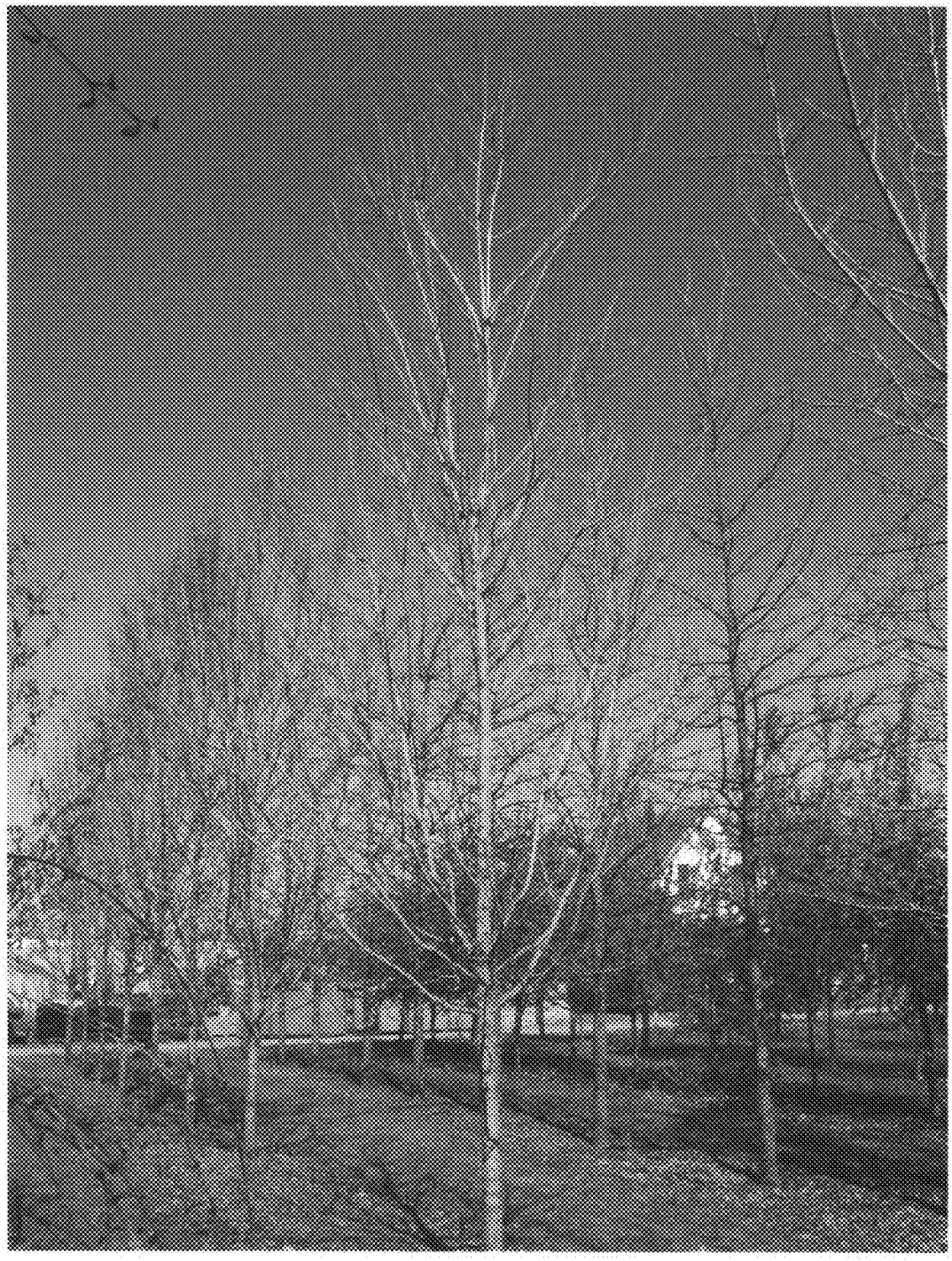
FIG. 2: Shows the branching structure and form of the original tree in winter, illustrating the straight trunk, straight leader, and upward branch angles.
Figure 3:
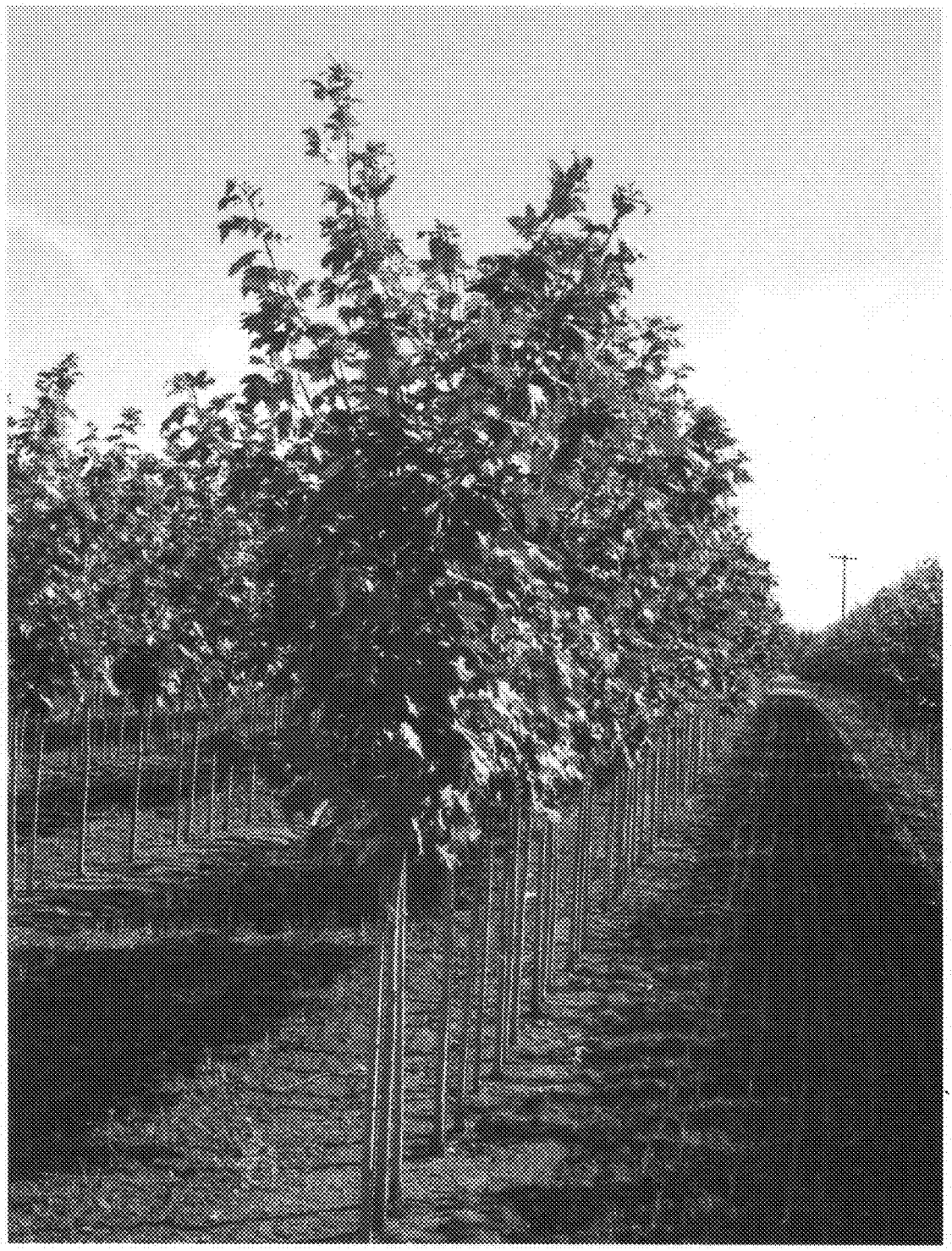
FIG. 3: Shows two year old trees in a nursery row, illustrating the straightness of form and upward angled branches of young asexually propagated trees.
Figure 4:
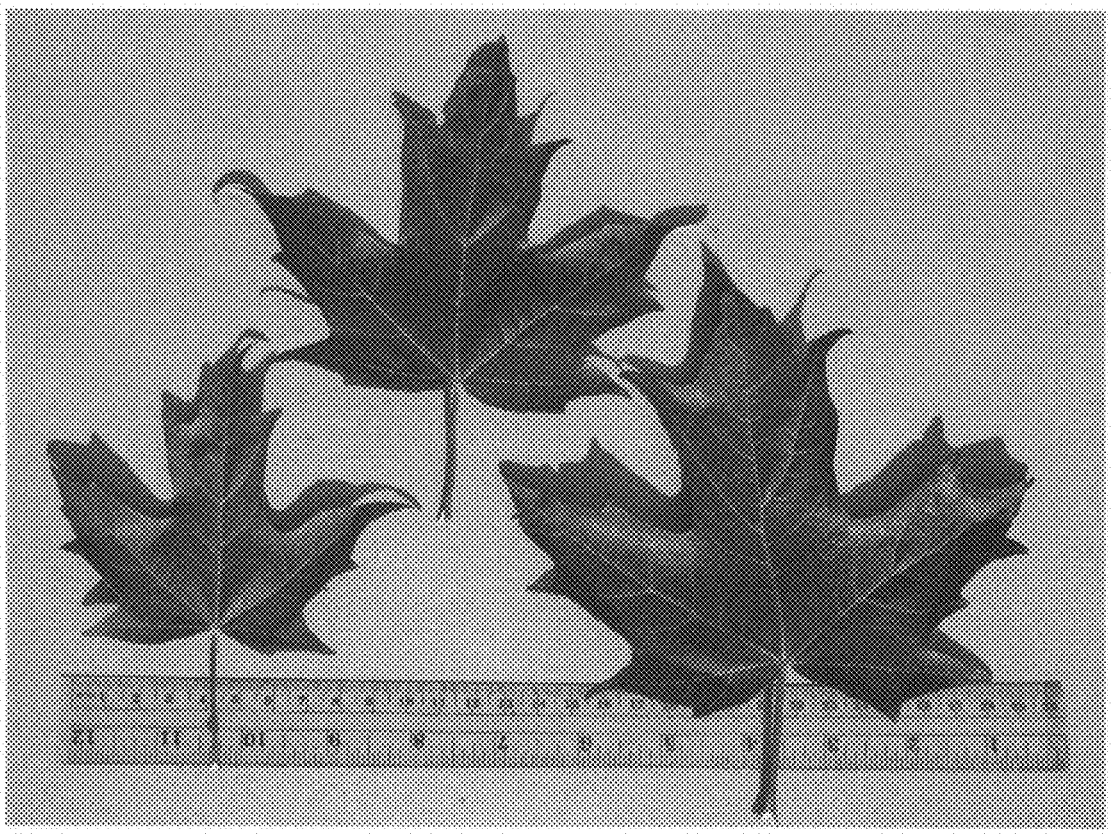
FIG. 4: Shows the top surface of the foliage in summer, illustrating the dark green color, satiny leaf sheen, leaf shape, and reddish upper surface of the petiole.
Figure 5:
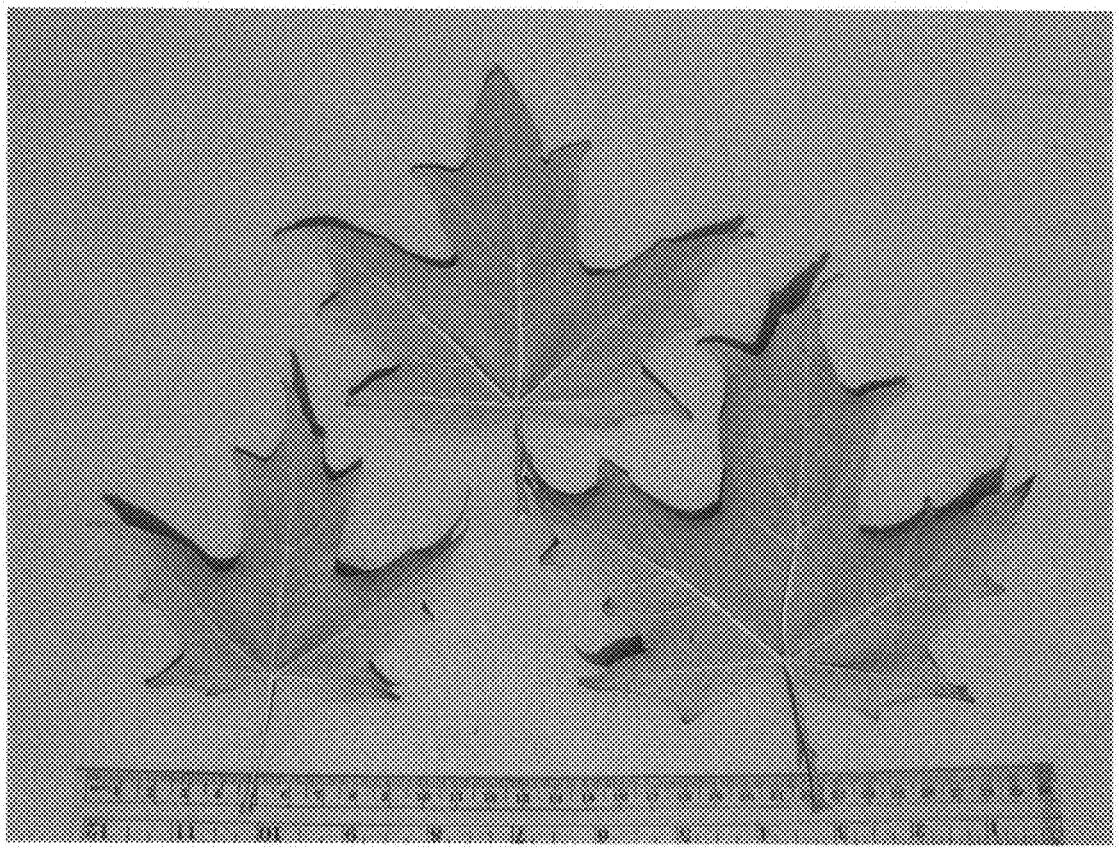
FIG. 5: Shows the lower surface of the foliage in summer, illustrating the lighter green underside of the leaf and the underside of the petiole.
Figure 6:
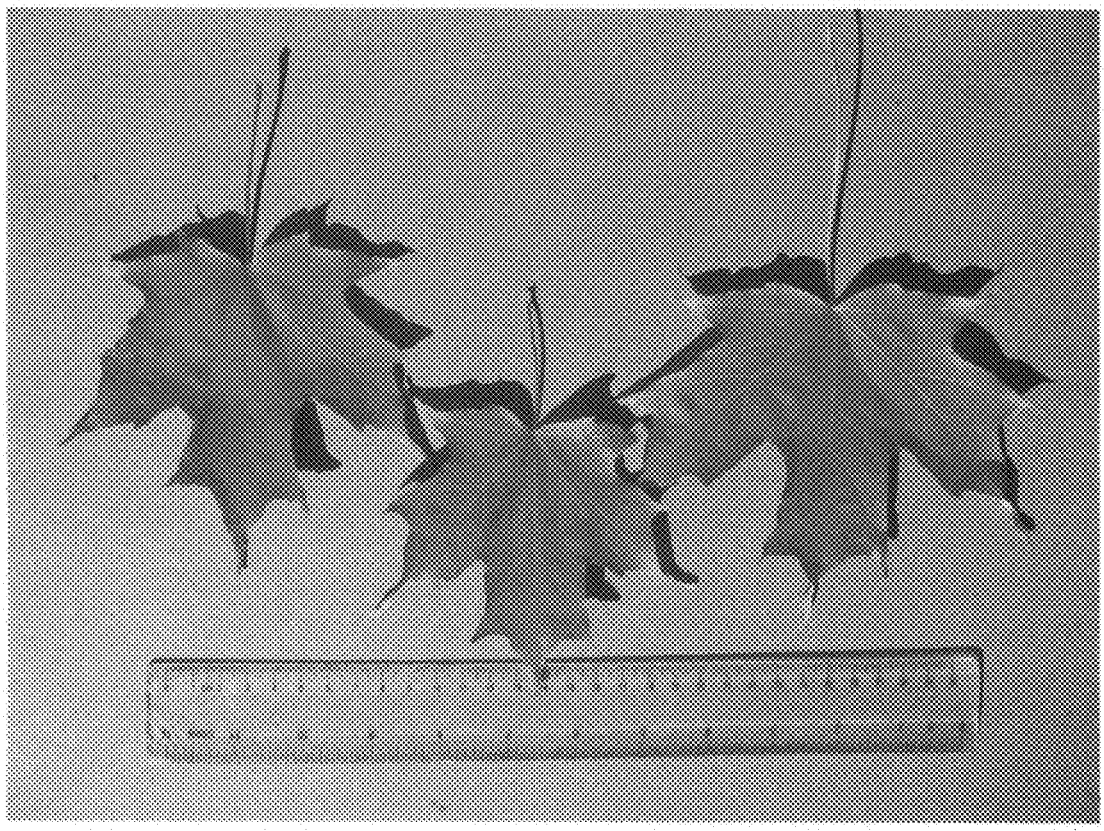
FIG. 6: Shows three typical leaves at the peak of fall color.
Figure 7:
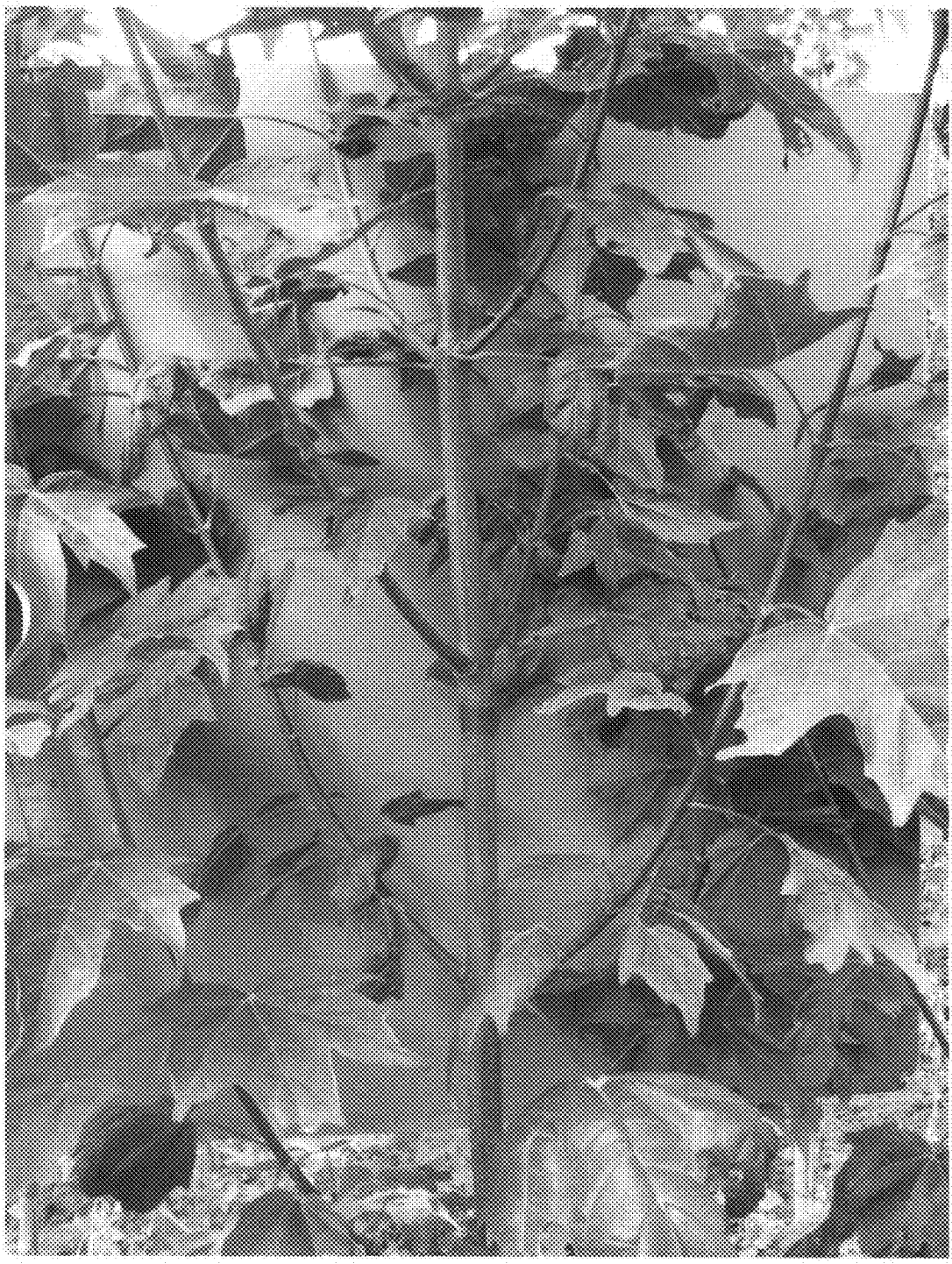
FIG. 7: Shows a close-up of a two year old nursery grown tree, illustrating the branch crotch angle and upward branch orientation on young propagated trees.
Figure 8:
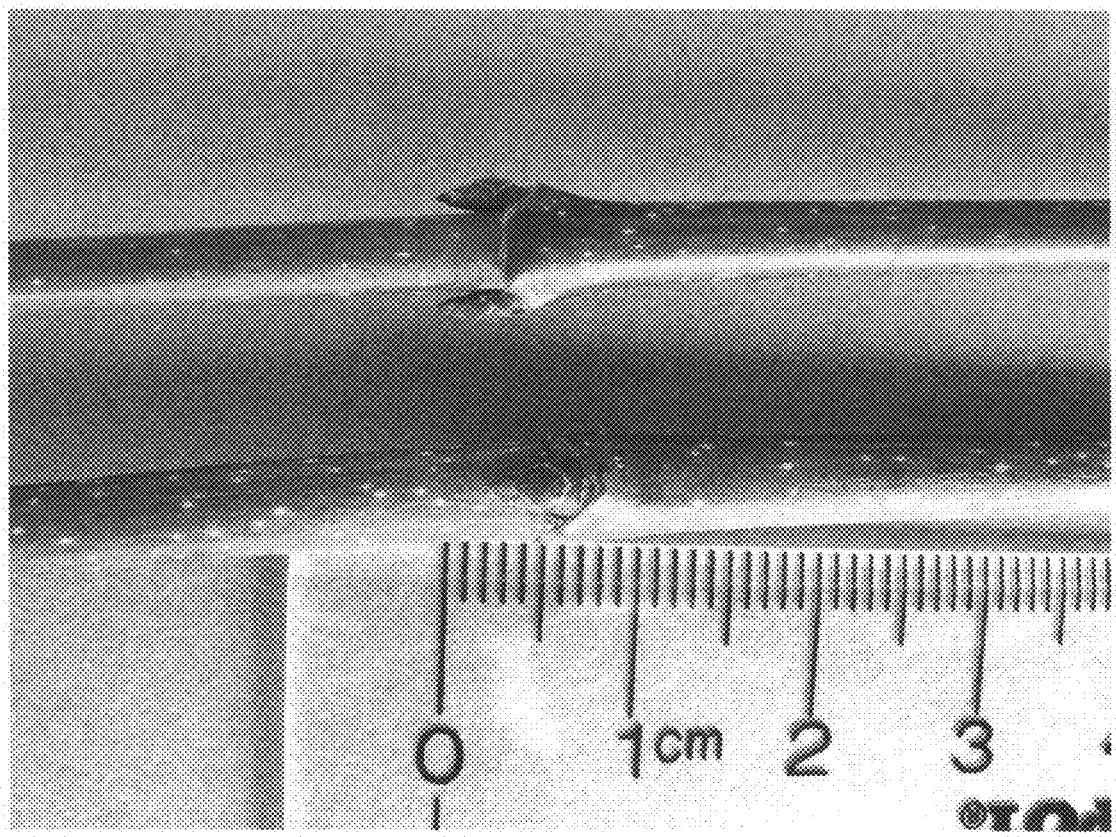
FIG. 8: Shows dormant buds and lenticels of one year old twigs, illustrating the shape of the buds and lenticels.

The following detailed description of the 'JFS-KW8' variety is based on observations of the original tree and one, two, and three year old progeny. The observed progeny were trees which were growing in Boring, Oreg.

The following is a detailed description of my new sugar maple tree with color descriptions using terminology in accordance with The Royal Horticultural Society (London) Colour Chart© 1986, except where ordinary dictionary significance of color is indicated.

Scientific name: *Acer saccharum* 'JFS-KW8'

Parentage:

*Seed parent.*—*Acer saccharum.*

*Pollen parent.*—*Acer saccharum.*

Tree:

*Overall shape.*—Upright oval to narrow oval.

*Height.*—9.8 meters at 13 years of age.

*Width.*—3.8 meters at 13 years of age.

*Caliper.*—12.5 cm at 10 cm height, 10.3 cm at 1 meter, at 13 years of age.

*Trunk.*—Straight, strongly upright, single stem with a very gradual taper.

*Trunk bark texture.*—Smooth.

*Trunk bark color.*—Immature bark color: Greyed-Green 196A to 197D. Mature bark color: Greyed-Green 196A to 197A. Lenticels: Not visible on trunk.

*Primary branches.*—Strongly and broadly upsweeping with typical crotch angles that are generally about 40° to 50°.

*Branch color.*—Young branches are Greyed-Orange 166A to 166B during the first winter, smooth and slightly lustrous, then become Greyed-Orange 177C, smooth, at 1 cm to 2 cm diameter.

*Branch lenticels.*—Orange-White 159B, 1 mm, rounded to mostly oval.

*Dormant buds.*—Narrowly conical with a sharply acute tip and imbricate scales. Greyed-Orange 166A to Brown 200A, except Greyed-Purple 183B at the base of the bud. Typically about 3 mm to 6 mm long by 2 mm to 3 mm wide.

*Bud break*—Very late to break bud in spring. Bud break averages April 22 under Boring, Oreg. conditions. Bud break is two weeks later than the average for the species.

*Internodes.*—In one observation, 7.1 cm average length on 1 yr tree at 1 meter height. 5.2 cm average length on branches of 2 year old trees. Hardiness: Has tolerated temperatures to 10 degrees F. without damage in Boring, Oreg. It has not been tested at lower temperatures, but it is believed to have Zone 4 cold hardiness similar to the species.

*Disease resistance.*—Moderately resistant to powdery mildew, an improvement over typical seedlings of the species. Otherwise, disease susceptibility is typical of the species.

Leaves: Except as otherwise noted, observations are from twenty vigorous growth leaves.

*Arrangement.*—Opposite.

*Type.*—Simple.

*Texture.*—Smooth; smoother than typical of the species.

*Sheen.*—Slightly satiny.

*Length.*—12 cm to 17 cm.

*Width.*—14 cm to 20 cm.

*Petioles.*—6 cm to 10 cm long×2 mm wide. Yellow-Green 145A on lower, shaded surface. Greyed-Red 181A on upper sun side.

*Overall shape.*—Palmate with five main lobes, deepest sinuses extend about half way to the center vein, lobe tips are acuminate.

*Margin.*—Smooth, with occasional acuminate minor lobe tips.

*Tip.*—Acuminate.

*Base.*—Cordate.

*Stipules.*—None.

*Spring leaf color.*—First emerging leaves are Yellow-Green 144B to Yellow-Green 152C.

*Summer leaf color.*—Upper leaf surface: Green 139A to Green 131A. Lower leaf surface: Grey-Green 191A. Vein: Yellow-Green 145A.

*Fall leaf color.*—Red 42A to Red 43A.

*Timing of fall leaf color.*—Average dates for original tree in Boring, Oreg.: Onset: October 5. Peak: October 17. Defoliation: November 1.

*Pubescence.*—Glabrous.

*Persistence.*—Tree is deciduous.

Flowers: No flowers have been observed as the original tree has not yet produced flowers.

Fruit: No fruit has been observed as the original tree has not yet produced seed.

Comparison to other varieties: The two most similar commercial cultivars of sugar maple are believed to be 'Bailsta' ("Sugar Maple Tree named 'Bailsta', U.S. Plant Pat. No. 11,119") and 'Green Mountain' ("Maple Tree," U.S. Plant Pat. No. 2,339, patent expired).

Compared to 'Bailsta', my new tree is taller, with one year trees of 'JFS-KW8' averaging 231 cm vs. 218 cm for 'Bailsta'. In addition, the sheen of the upper leaf surface of 'JFS-KW8'is slightly satiny while that of 'Bailsta' is slightly glossy to glossy. Fall leaf color of 'Bailsta' typically has a range of colors of yellow, orange and red.

Compared to 'Green Mountain', the slightly satiny upper leaf surface of 'JFS-KW8' is easily distinguished from the dull leathery leaf surface of 'Green Mountain'. In addition, 2 year old 'Green Mountain' trees have wide branch crotch angles (50°-80°) while 'JFS-KW8' has moderate branch crotch angles that are typically 40°-50°. Branch orientation of 2 year trees of 'Green Mountain' is wider (45°-60° measured 30 cm from trunk) while that of 'JFS-KW8' in narrower and more upsweeping (typically 30°-40° measured 30 cm from trunk).

Comparison to the species: My new variety is straighter, taller, more upright, and moderately narrower in form than the species. The 13 year old original tree is best described as narrowly oval to oval in shape, while typical trees of the species are broadly oval to round at the same age. Measurement of propagated one and two year old trees of my new variety and seedlings of the species confirm this form difference. This and other differences are detailed in Table 1 below.

TABLE 1

| Feature: | 'JFS-KW8' | Seedling |
|---|---|---|
| Tree shape (13 year age) | Narrow oval to oval | Broadly oval to rounded |
| Summer leaf color, upper | Green 139A to 131A | Yellow-Green 147A |
| Summer leaf color, lower | Greyed-Green 191A | Greyed-Green 194B |
| Internode length, 1 year age at 1 meter height | 7.1 cm | 11.7 cm |
| Branch crotch angle, 2 year age | 40°-50°, consistent | 20°-80°, variable |
| Branch orientation angle, 30 cm from trunk, 2 year age | 30°-40°, consistent, upward | 10°-90°, highly variable |
| Straightness; variance of leader from vertical at 2 meter height, 1 year age | 9° | 24° |

TABLE 1-continued

| Feature: | 'JFS-KW8' | Seedling |
|---|---|---|
| Spring bud break | Late, averages April 22 in Boring, OR | Normal, averages April 8 in Boring, OR |

I claim::

1. A new and distinct variety of sugar maple tree, substantially as herein shown and described.

* * * * *